(12) United States Patent
    Blue

(10) Patent No.: US 9,513,208 B2
(45) Date of Patent: Dec. 6, 2016

(54) FILTER CAKE DRAG TESTER

(71) Applicant: M-I L.L.C., Houston, TX (US)

(72) Inventor: Aaron Blue, Houston, TX (US)

(73) Assignee: M-I L.L.C., Houston, TX (US)

( * ) Notice: Subject to any disclaimer, the term of this patent is extended or adjusted under 35 U.S.C. 154(b) by 141 days.

(21) Appl. No.: 14/140,685

(22) Filed: Dec. 26, 2013

(65) Prior Publication Data
    US 2014/0290330 A1   Oct. 2, 2014

Related U.S. Application Data

(60) Provisional application No. 61/747,721, filed on Dec. 31, 2012.

(51) Int. Cl.
    *G01N 19/02* (2006.01)
    *G01N 3/56* (2006.01)

(52) U.S. Cl.
    CPC ............. *G01N 19/02* (2013.01); *G01N 3/567* (2013.01)

(58) Field of Classification Search
    CPC ................................ G01N 19/02; G01N 3/567
    USPC .................................................. 73/9
    See application file for complete search history.

(56) References Cited

U.S. PATENT DOCUMENTS

2010/0126252 A1* 5/2010 Bailey ................ G01N 11/14
                                                    73/54.28

OTHER PUBLICATIONS

OFI Lubricity Tester, http://www.ofite.com/products/112-00.asp.
"Recommended Practice for Field Testing Oil-Based Drilling Fluids", API Recommended Practice 12B-2, Fifth Edition, 2012, 156 pages.

* cited by examiner

*Primary Examiner* — John Fitzgerald
*Assistant Examiner* — Rodney T Frank
(74) *Attorney, Agent, or Firm* — Sara K. M. Hinkley

(57) ABSTRACT

A method that includes pulling a sled disposed on a trough across a first filtercake at a constant speed, measuring a force versus distance or time based on the pulling; and outputting a frictional force curve is described. An apparatus that includes a base, a pulley attached to the base, a trough attached to the base, a sled disposed on the trough, a cable connecting the pulley and the sled, the cable connected to an arm capable of being moved at a constant speed, and a system to measure the force required to move the sled is also described.

12 Claims, 5 Drawing Sheets

FILTER CAKE DRAG TESTER

CROSS REFERENCE TO RELATED APPLICATIONS

This application claims the benefit of U.S. Provisional Application No. 61/747,721, filed 31 Dec. 2012.

BACKGROUND

In the drilling of boreholes such as oil or gas wells, a drilling fluid (hereinafter referred to as "drilling mud") is circulated through the well during drilling in order to, inter alia, remove drilled cuttings, balance the pressure of formation fluids to prevent influxes and maintain the stability of the borehole. In order to provide the required density and viscosity, the mud can include certain solids such as barite and bentonite as well as solids derived from the drilling action. When drilling oil and gas wells, it is quite common to encounter subterranean formations which are porous. If the hydrostatic pressure of the drilling fluid is greater than the pressure of fluids in such formations, mud will penetrate the formation. Generally the pore size of such formations is sufficient to admit the liquid components and very fine solids but to filter out the other solids such as barite or bentonite. These filtered solids form on the borehole wall as a filtercake. This filtercake grows and compacts until the differential pressure is balanced by the stress in the filtercake.

The filtercake has a much lower permeability than the formation. Filtercake can therefore be useful as it acts as a barrier to prevent fluid loss from the drilling mud to the formation. A number of was of forming filter cakes are known in the art, including the use of bridging particles, cuttings created by the drilling process, polymeric additives, and precipitates. Filtercakes, therefore, have different compositional structures, based on the additives, base fluid, and cuttings.

If a filtercake becomes too thick, problems can occur. For example, filtercakes can be a significant contributor to differential sticking: if the drill string or bottomhole assembly (BHA) is allowed to rest against the wellbore wall, the filtercake can continue to grow around the contact point, and must be yielded in order to free the BHA. Emphasis has therefore been placed on developing thin, highly impermeable but weak filtercakes, which minimize their contribution to severity of differential sticking, and also ease clean-up in the reservoir section.

During the drilling of a borehole through underground formations, the drill string assembly undergoes considerable sliding contact with both the steel casing and rock formations. This sliding contact results primarily from the rotational and axial movements of the drill string assembly in the borehole. Friction between the moving surface of the drill string assembly and the stationary surfaces of the casing and formation creates considerable drag on the drill string and results in excessive torque and drag during drilling operations. The problem caused by friction is inherent in any drilling operation, but it is especially troublesome in directionally drilled wells or extended reach drilling (ERD) wells. Directional drilling or ERD is the intentional deviation of a wellbore from the vertical. In some cases the angle from the vertical may be as great as ninety degrees from the vertical. Such wells are commonly referred to as horizontal wells and may be drilled to a considerable depth and considerable distance from the drilling platform. Friction between the drill string assembly and the wellbore walls is also observed when the drill bit (and assembly) is pulled out of hole.

In all drilling operations, the drill string assembly has a tendency to rest against the side of the borehole or the well casing, but this tendency is much greater in directionally drilled wells because of the effect of gravity. As the drill string increases in length or degree of vertical deflection, the amount of friction created by the rotating drill string assembly also increases. To overcome this increase in friction, additional power is required to rotate the drill string assembly. In some cases, the friction between the drill string assembly and the casing wall or borehole exceeds the maximum torque that can be tolerated by the drill string assembly and/or maximum torque capacity of the drill rig and drilling operations must cease. Consequently, the depth to which wells can be drilled using available directional drilling equipment and techniques is limited.

One method for reducing the friction caused by the contact between the drill string assembly and casing (in case of a cased hole) or borehole (in case of an open hole) is improving the lubricity of drilling muds. In industry drilling operations, attempts have been made to reduce friction through, mainly, using water and/or oil based mud solutions containing various types of expensive and often environmentally unfriendly additives. Diesel and other mineral oils are also often used as lubricants, but there is a problem with the disposal of the mud. Certain minerals such as bentonite are known to help reduce friction between the drill string assembly and an open borehole. Materials such as TEFLON® have been used to reduce friction, however these lack durability and strength. Other additives include vegetable oils, asphalt, graphite, detergents and walnut hulls, but each has its own limitations.

SUMMARY OF THE DISCLOSURE

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method that includes pulling a sled disposed on a trough across a first filtercake at a constant speed, measuring a force versus distance or time based on the pulling; and outputting a frictional force curve.

In another aspect, embodiments disclosed herein relate to a method that includes pulling a sled across a first filtercake at a constant speed, measuring a force versus distance or time, outputting a first frictional force curve, creating a second filtercake, pulling a sled across the second filtercake, measuring a force versus distance or time, outputting a second frictional force curve, comparing the first frictional force curve and the second frictional force curve, and selecting a drilling fluid based on the comparing.

In another aspect, embodiments disclosed herein relate to an apparatus that includes a base, a pulley attached to the base, a trough attached to the base, a sled disposed on the trough, a cable connecting the pulley and the sled, the cable connected to an arm capable of being moved at a constant speed, and a system to measure the force required to move the sled.

Other aspects and advantages of the claimed subject matter will be apparent from the following description and the appended claims.

DETAILED DESCRIPTION

In one aspect, embodiments disclosed herein relate to methods and apparatuses for testing the frictional forces resulting from the interaction of drilling equipment with a filtercake. More specifically, embodiments disclosed herein relate to methods and apparatuses for testing the static frictional force encountered by a drill string (such as when changing the bit) when pulled against a filtercake. Various filtercakes can be analyzed to determine a friction profile and the overall lubricity (or lack thereof) of the filtercake formed by a given fluid.

A suitable filtercake for use in embodiments disclosed herein may be made in accordance with the methodology disclosed in standard high temperature high pressure (HTHP) fluid loss tests, such as those according to the specifications of the American Petroleum Institute (API), as described in "Recommended Practice Standard Procedure for Field Testing Oil-Based Drilling Fluids," API Recommended Practice 13B-2 Third Edition, February 1998, Section 5.2.1 to 5.2.3; and "Recommended Practice Standard Procedure for Field Testing Water-Based Drilling Fluids," API Recommended Practice 13B-1 Second Edition, September 1997, Section 5.3.1 to 5.3.2.

The API test employs a pressurized cell fitted with a standard hardened filter paper as a filtration medium. The filtration behavior of the drilling mud is determined with a standard pressure differential across the filter paper of 500 psi (3.45 M Pa). A filter cake is allowed to build up on the filter paper for 30 minutes. The filtercake can then be removed and used with the testing apparatus of the present disclosure. Various fluids may be used to create a number of various filtercakes for testing purposes. Further, the API test is a single way to form a filter cake that is often used in the drilling fluid industry; however, there is no limitation on the way in which a filtercake may be formed. Rather, one of ordinary skill in the art would appreciate that a filter cake may be built on any type of medium through which a fluid phase can pass and allow for the build-up of the fluid components as a cake on the medium. A standardized set of procedures may allow for fewer variations in the filtercake properties between filtercakes. For example, when evaluating the potential effect of different fluid components on the friction between the filtercake and a drill string assembly, use of a standardized filtercake test may allow for a more accurate assessment of the effect of the fluid components on the filtercake and friction generated.

Figure 1:
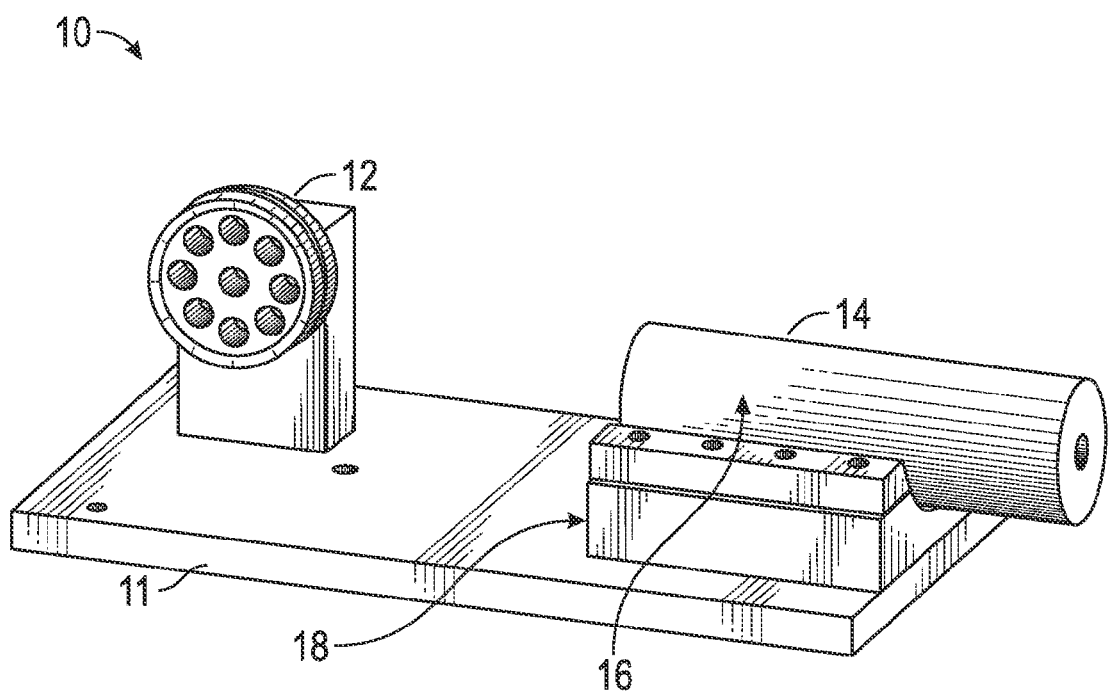
FIG. 1 shows components of a friction tester in accordance with an embodiment of the disclosure.

Turning to FIG. 1, a partial view of one embodiment of a friction tester 10 for use in testing the frictional forces in filtercake/drill string interaction is shown. As illustrated, components of a friction tester 10 include a pulley 12, attached to a base 11. A trough 18 is also attached to base 11. A sled 14, which emulates a drilling component such as a length of drilling pipe, is placed on the trough 18. A filtercake on filter paper 16 is disposed on the trough 18 between the sled 14 and trough 18. The filter paper 16 is held in place by a retaining member (not shown), such as a clamp. The retaining member may be any suitable device which can hold the filter paper in place.

The sled 14 may be formed from a variety of drilling grade steels, or may be formed from any suitable material that may be used in drilling operations. Filtercake on filter paper 16 is clamped into place so that it remains rigidly attached to the trough 18. Trough 18 may be formed from the same material as sled 14, or can be formed from a different material.

While a filtercake on filter paper 16 is shown, those having ordinary skill in the art will appreciate that the filtercake may also be formed on other devices used to measure the properties of filtercakes, such aloxite disks. In addition, multiple sheets of filter paper with filtercakes may be used to increase the surface area of filtercake to interact with sled 14. The geometric properties of the trough 18 or the sled 14 may be modified to have a "lip," (i.e., a raised portion that the sled 14 must pass over) have surface roughness, or other geometric properties to better approximate the real world conditions. In addition, the filtercake could be formed onto the sled 14, and pulled against the trough 18. Moreover, while sled 14 is shown as a generally cylindrical tube, there is no limitation imparted on the scope of the present disclosure by this shape.

Figure 2:
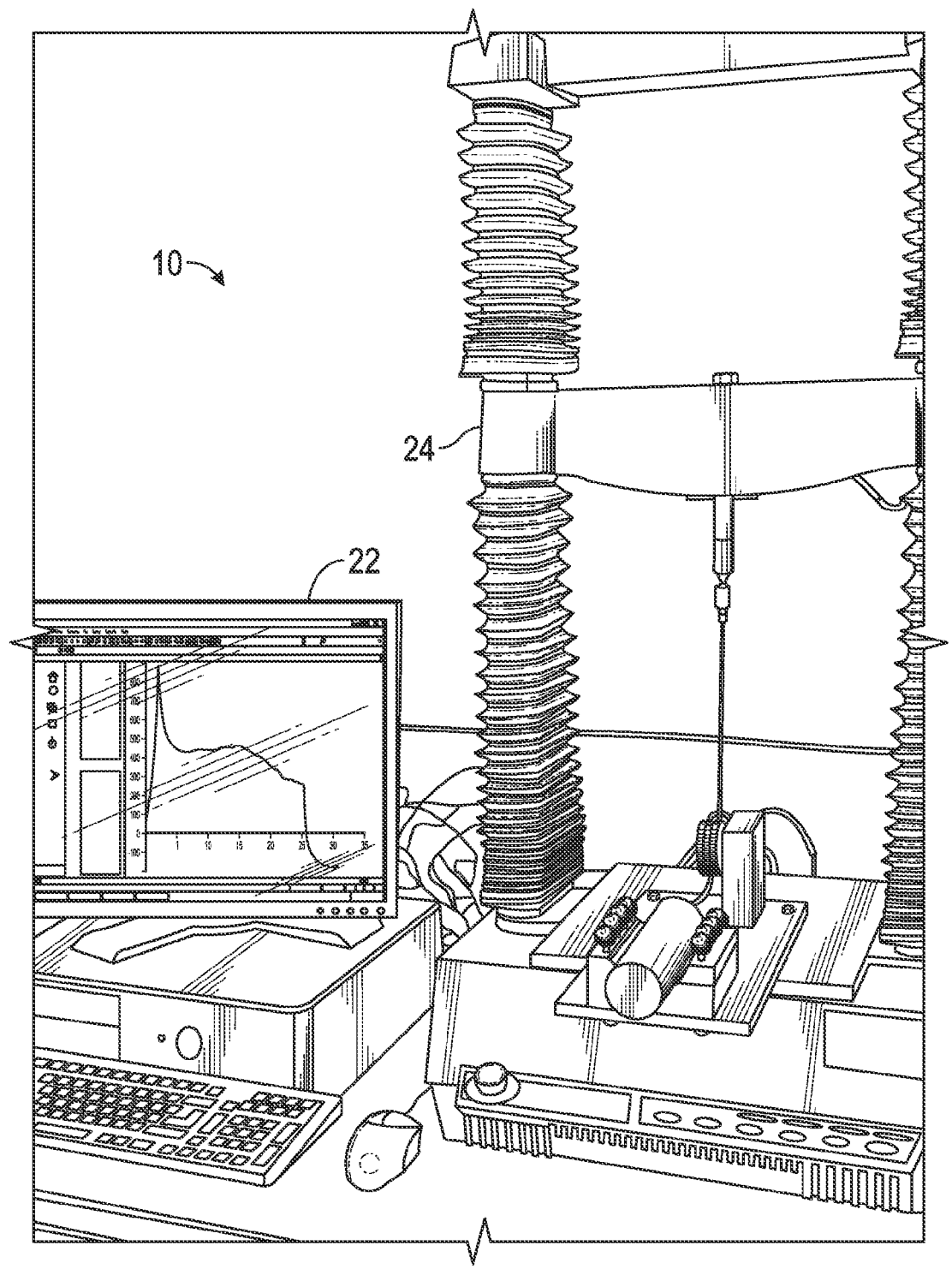
FIG. 2 shows an assembled friction tester in accordance with an embodiment of the disclosure.

Turning to FIG. 2, friction tester 10, which is modified from a Texture Analyzer (available from Stable Micro Systems, London, England), is shown with all components in place. Cable 20 is connected to arm 24, and is run through pulley 12 and attached to sled 14. Friction tester 10 is operatively connected to a computer 22, which displays the results of the test. The friction tester 10 includes a linear transducer placed, for example which outputs a converted signal relative to the range of displacement that has taken place and a force transducer (such as a strain gage), to measure the force applied over a given distance. In operation, a speed at which the arm 24 moves vertically is set, and as the arm 24 is displaced, cable 20, through pulley 12, pulls sled 14 laterally through trough 18 and across the filtercake on filter paper 16. In one embodiment, the trough 18 has a length of four inches, and the sled 14 weighs four pounds.

Those having ordinary skill in the art will appreciate that while one friction tester 10 is shown, any suitable system for measuring the force required to move the sled 14 may be used. While linear transducers and force transducers are disclosed, other suitable techniques for producing a force versus distance curve may be employed. In this embodiment, the linear displacement is measured, in order to assure that the filtercake remains in place against the sled 14. However, embodiments are not so limited, as the system may be arranged in a vertical fashion as well.

One advantage of the present disclosure is the ability to change aspects of various components to better emulate real-world situations. For example, for a case where pipe is being removed from a deviated well, the friction tester may be modified such that either the pulley or trough height is modified to create an angle of inclination between the two components. This angle may be selected to match the angle for a drilled well. In other words, rather than pulling the sled normal to the arm, the sled may be pulled at an angle that is equivalent to a drilled angle. One of ordinary skill in the art will appreciate that the depth of the trough could also be similarly changed to achieve the same result. In one embodiment, therefore, the friction tester includes an adjustable height pulley, which can be raised or lowered as desired.

Additionally, the geometric or material aspects of one or more components may be modified to better emulate real-world conditions. For example, the surface roughness of either the sled or the trough may be increased. The trough diameter or length may be increased or decreased. The overall shape of the trough may be modified to be less cylindrical. Additionally, the sled may be modified to have different materials, dimensions, weight, and roughness, among other considerations.

Figure 3:
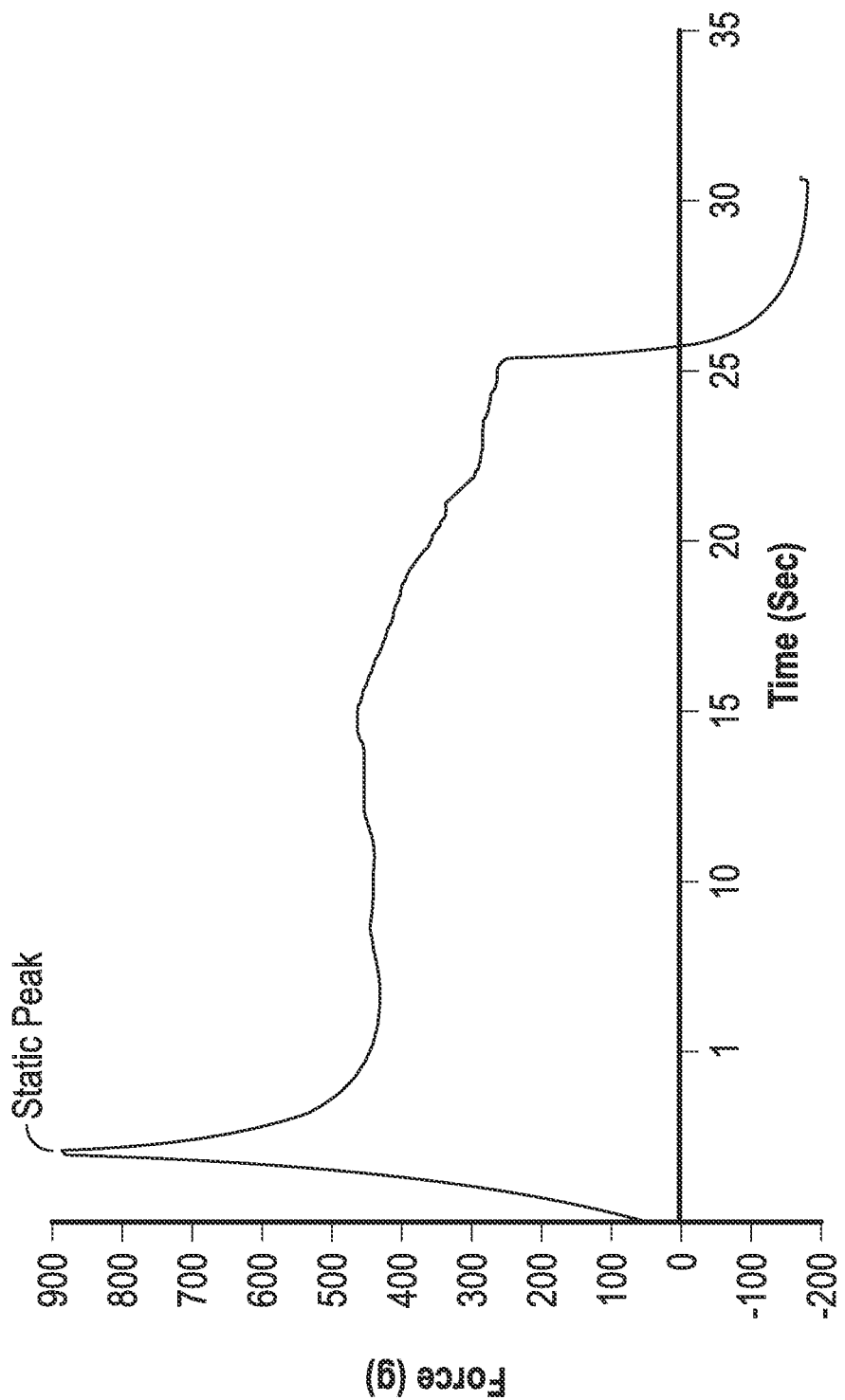
FIG. 3 is a Force versus Time curve.

FIG. 3 illustrates the result of one test as a force versus time curve. As can be seen from FIG. 3, in order to overcome the initial static friction between sled 14 and filtercake on filter paper 16, a high initial force is required. After that initial static friction is overcome, the force required to move sled 14 decreases significantly (which is a measure of the dynamic friction), and has a relatively flat progression until the test concludes.

This embodiment, therefore, provides a user with the measure of both the static and dynamic frictional forces encountered. A user can then repeat the test by modifying the filtercake (i.e., changing the fluids and/or additives used to create the filtercake), and looking at how the force versus distance curve is modified. In one embodiment, for example, a lubricant can be added to the mud, and the resultant effect on the force versus distance curve can be analyzed. In addition, the solids content of the mud may be increased or decreased to change the thickness of the filtercake. By selecting various lubricants the curve can be modified to achieve a desired result, such as reducing, or eliminating the static peak, to eliminate the variability in the force required to pull a drillstring out of the hole.

Figure 4:
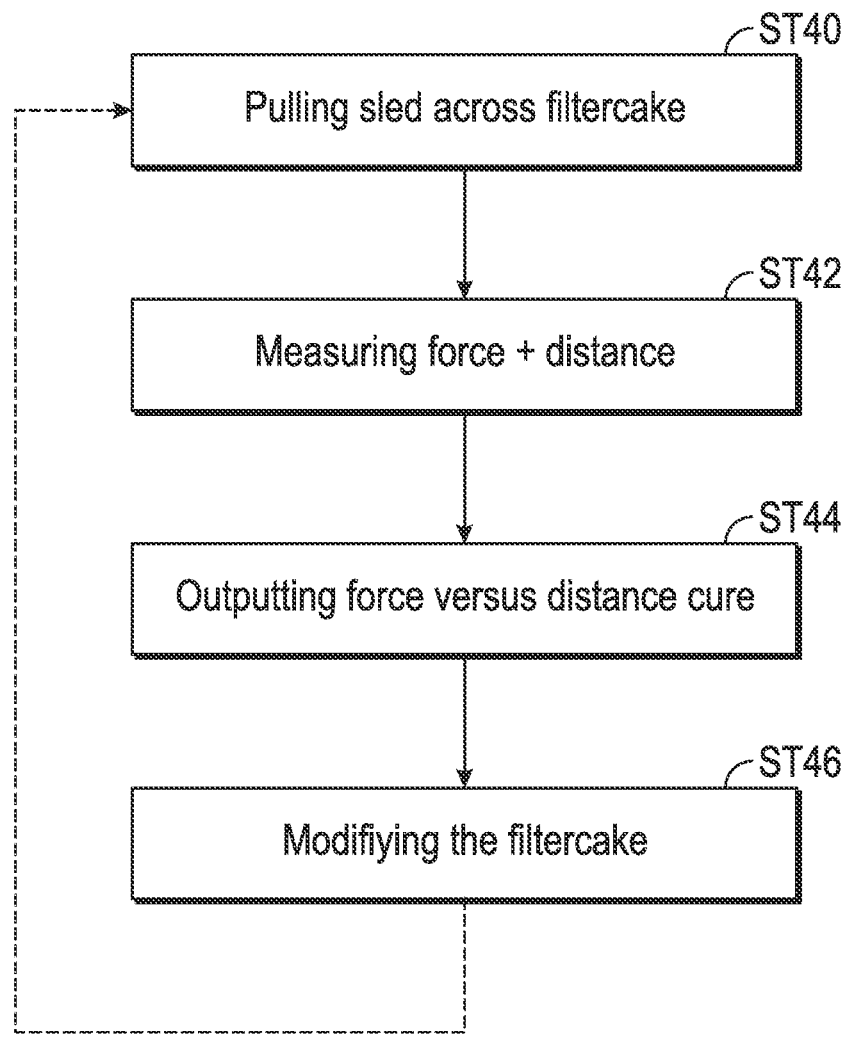
FIG. 4 is a flowchart in accordance with an embodiment of the disclosure.
Figure 5A:
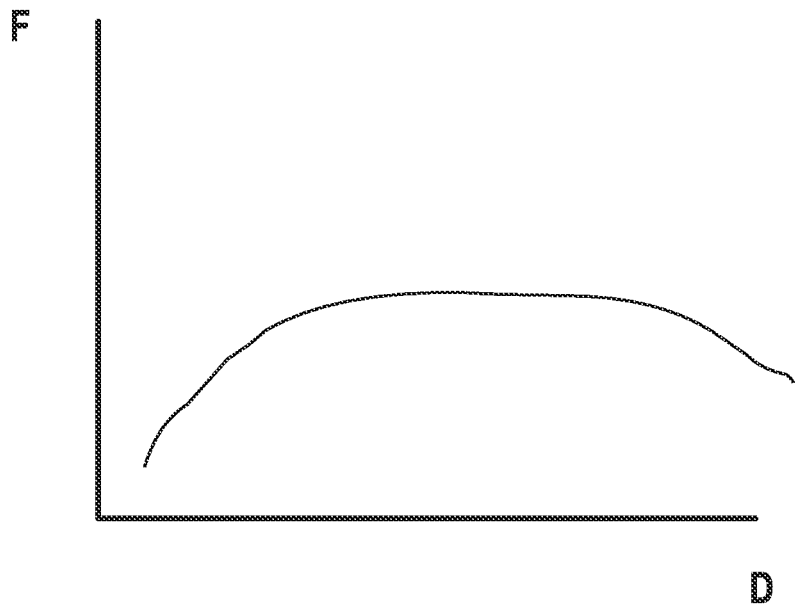
FIG. 5A is a Force versus Distance curve.
Figure 5B:
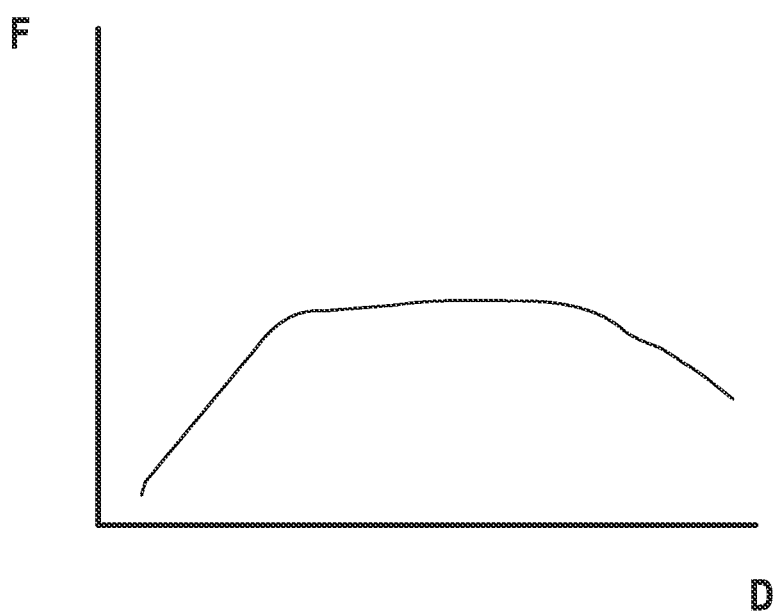
FIG. 5B is a Force versus Distance curve.

FIG. 4 shows a flowchart in accordance with an embodiment of the disclosure. In FIG. 4, a sled is pulled across a filtercake ST40. The force is measured, with a force gauge, and the distance is measured with a linear transducer ST42. The force versus distance curve is then output ST44. The filtercake may then be modified ST46, and the process repeated. As noted above, modifying the filtercake may include adding a lubricant, changing the solids content, changing the base fluid, or any other technique to create or change the properties of a filtercake. This process may be repeated until an optimized curve is created. An optimized curve, for example, may be one with a reduced static peak, or have a flat dynamic portion. FIGS. 5A and 5B illustrate two curves that may be preferable to the one shown in FIG. 3. Further, it is noted that FIG. 3 shows force versus time, while FIGS. 5A and 5B show force versus distance. Because the speed of the sled is constant, the 'force vs time' and 'force vs distance' plot will be the same in this embodiment. What FIGS. 5A and 5B demonstrate is a static frictional force that is nearly equal to the dynamic frictional force. Other aspects may be modified to produce a desired curve.

One of ordinary skill in the art would appreciate that raw data may be measured as distance or time, and may be converted to the other based on the speed of the pulling arm. Further, it is also within the scope of the present disclosure that the data may be considered in the form of a resistant force versus applied force curve. In any situation, the data may show the transition between static friction and kinetic or dynamic friction, and comparison of multiple curves may demonstrate a filtercake with which less friction or drag is created when a drill string assembly is pulled or pushed against the filtercake. Thus, the present disclosure may generally relate to formation and comparison of frictional force curves, which may include any type of frictional force curve, including force versus distance, force versus time, resistance force versus applied force, as well as any other type of curve that will indicate static and kinetic or dynamic frictional forces.

Based on this methodology, a number of filtercakes can be analyzed to determine which have the least force required to pull the drillstring, or have the most constant force, for example. Advantageously, embodiments of the present invention provide a quick and low cost method of testing the frictional forces for a variety of filtercakes, which can allow for the selection of improved fluids when drilling a well. Also, embodiments disclosed herein provide a way to test the lubricating properties of various additives, by looking at their resultant impact on the force versus distance curves generated by embodiments disclosed herein.

Also advantageously, embodiments of the present disclosure may provide an ability to predict the behavior of filtercakes prior to pulling the drillstring out of a hole. For example, a drilling company could request an analysis of the filtercake to determine whether they are likely to see a "stick" situation (where drilling pipe is caught by the static frictional force), to determine whether they need to pump additional lubricating material downhole to avoid this situation. Thus, embodiments disclosed herein can be used to assist with current drilling conditions, by predicting the behavior of filtercakes to allow a drilling company to make a decision about which additional additives should be used.

Although a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed:

1. A method comprising:
    pulling a sled disposed on a trough across a first filtercake at a constant speed;
    measuring a force versus distance or time based on the pulling; and
    outputting a frictional force curve.

2. The method of claim 1, further comprising:
    repeating the pulling, measuring, and outputting with at least one other filtercake.

3. The method of claim 2, wherein the repeating occurs until an optimized force versus distance curve is output.

4. The method of claim 1, further comprising:
    modifying the filtercake by increasing the thickness of the filtercake.

5. The method of claim 2, wherein the at least one other filtercake comes from a fluid having a different composition than the first filtercake.

6. The method of claim 1, further comprising: modifying a property of the sled, wherein the property comprises at least one selected from the group consisting of surface roughness, shape, length, diameter, weight, and a material that the sled is formed from.

7. A method comprising:
    pulling a sled across a first filtercake at a constant speed;
    measuring a force versus distance or time;
    outputting a first frictional force curve;
    creating a second filtercake;

pulling a sled across the second filtercake;
measuring a force versus distance or time;
outputting a second frictional force curve;
comparing the first frictional force curve and the second frictional force curve; and
selecting a drilling fluid based on the comparing.

8. An apparatus comprising:
a base;
a pulley attached to the base;
a trough attached to the base;
a sled disposed on the trough;
a retaining member for holding a filtercake between the sled and the trough;
a cable connecting the pulley and the sled, the cable connected to an arm capable of being moved at a constant speed; and
a system to measure the force required to move the sled.

9. The apparatus of claim 8, wherein the pulley has an adjustable height.

10. The apparatus of claim 8, further comprising a computer operatively connected to the apparatus.

11. The apparatus of claim 8, wherein the trough is adjustable.

12. The method of claim 1, further comprising: modifying a property of the trough, wherein the property comprises at least one selected from the group consisting of surface roughness, shape, length, diameter, weight, and a material that the trough is formed from.

\* \* \* \* \*